United States Patent [19]
Auth et al.

[11] Patent Number: 5,314,407
[45] Date of Patent: May 24, 1994

[54] CLINICALLY PRACTICAL ROTATIONAL ANGIOPLASTY SYSTEM

[75] Inventors: David C. Auth, Redmond; Michael J. Intlekofer, Bellevue; Michael W. Slota, Bothell; John S. Hinchcliffe, Seattle; Thomas J. Clement, Redmond, all of Wash.

[73] Assignee: Heart Technology, Inc., Bellevue, Wash.

[21] Appl. No.: 917,923

[22] Filed: Jul. 21, 1992

Related U.S. Application Data

[63] Continuation of Ser. No. 806,828, Dec. 6, 1991, abandoned, which is a continuation of Ser. No. 646,519, Jan. 25, 1991, abandoned, which is a continuation of Ser. No. 462,899, Dec. 29, 1989, abandoned, which is a continuation of Ser. No. 135,495, Dec. 21, 1987, abandoned, which is a continuation of Ser. No. 930,842, Nov. 14, 1986, abandoned.

[51] Int. Cl.$^5$ ............................................. A61B 17/22
[52] U.S. Cl. ...................................... 604/22; 606/159
[58] Field of Search ................ 604/22; 606/159, 180; 128/751-755

[56] References Cited
U.S. PATENT DOCUMENTS

| | | | |
|---|---|---|---|
| 4,002,169 | 1/1977 | Cupcer | 128/305 X |
| 4,445,509 | 5/1984 | Auth | 128/305 |
| 4,622,503 | 11/1986 | Sundblom et al. | 128/305 X |

Primary Examiner—Michael H. Thaler
Attorney, Agent, or Firm—Cowan, Liebowitz, & Latman

[57] ABSTRACT

The present invention is a clinically practical, rotational angioplasty system which employs a unique rotary ablative device for mechanically abrading, and thereby removing, lesions from within a patient's vessels. The device has a gas driven prime mover connected, via a hollow helical drive assembly, to an ellipsoidal, rotating, ablative burr which is used for the actual recanalization of the patient's vessel. The burr is provided with a central opening therethrough, which, together with the hollow drive assembly, permits the burr and drive assembly to be threaded over a guide wire similar to the type conventionally used in a catheterization procedure. The drive assembly is located within a hollow sheath which prevents the rotating drive assembly from contacting the inner walls of a patient's vessel.

32 Claims, 4 Drawing Sheets

CLINICALLY PRACTICAL ROTATIONAL ANGIOPLASTY SYSTEM

This application is a continuation of U.S. patent application Ser. No. 806,828, filed Dec. 6, 1991, now abandoned which in turn is a continuation of U.S. patent application Ser. No. 646,519, filed Jan. 25, 1991, now abandoned, which in turn is a continuation of U.S. patent application Ser. No. 462,899, filed Dec. 29, 1989, now abandoned, which in turn is a continuation of U.S. patent application Ser. No. 135,495, filed Dec. 21, 1987, now abandoned, which in turn is a continuation of U.S. patent application Ser. No. 930,842, filed Nov. 14, 1986, now abandoned.

BACKGROUND OF THE INVENTION

The present invention relates to an invasive medical apparatus for restoring patency to occluded vessels. In particular, the present invention is a clinically practical rotational angioplasty system.

In U.S. Pat. No. 4,445,509 entitled METHOD AND APPARATUS FOR REMOVAL OF ENCLOSED ABNORMAL DEPOSITS which issued to David C. Auth on May 1, 1984, the concept of flexibly conveying high-speed rotational energy through a catheter which can, in turn, be threaded into an artery obstructed by pathological material was described. In the same patent, the concept for differential cutting was introduced as a means of aggressively removing hard deposits while sparing soft normal tissue.

In U.S. Pat. No. 4,646,736 entitled TRANSLUMINAL THROMBECTONY APPARATUS issued Mar. 3, 1987, the concept of winding, and thereby ensnaring, fibrin to destructure and dissolve an intravascular clot, and a machine designed for that purpose, was described. In U.S. patent application Ser. No. 816,190, entitled TRANSLUMINAL MICRODISSECTION DEVICE, filed Jan. 6, 1986, now abandoned the concept of producing non-clogging fragments of soft or hard tissue was described.

In U.S. Pat. No. 4,679,557 entitled ELECTRODYNAMIC TRANSLUMINAL ANGIOPLASTY SYSTEM, issued Jul. 14, 1987 by Eric A. Opie, et al. a complete system, employing a prime mover, a control device, and an angioplasty cutting head of the type described in U.S. Pat. No. 4,445,509, is described. That system, though, was designed with a frictional drive prime mover, and it is not suitable for use with a very high speed abrasive burr, of the type described in Ser. No. 816,190. Accordingly, a single, clinically practical device, having a high speed drive, a rotating, ablative burr, a suitable controller, and the ability to remove fibrin and clear clots, which could be conveniently used in a sterilized environment, would be highly desirable.

SUMMARY OF THE INVENTION

The present invention is a clinically practical, rotational angioplasty system which employs a unique rotary ablative device for mechanically abrading, and thereby removing, lesions from within a patient's vessels. The device, called a "Rotablator" by its inventors, is comprised of a gas driven prime mover having an integrated water pump and fiberoptic tachometer. The prime mover is connected, via a hollow helical drive assembly, to an ellipsoidal, rotating, abrasive burr which is used for the actual recanalization of the patient's vessel. The burr is provided with a central opening therethrough, which, together with the hollow drive assembly, permits the burr and drive assembly to be threaded over a guide wire similar to the type conventionally used in a catheterization procedure.

The drive assembly is located within a hollow sheath which prevents the rotating drive assembly from contacting the inner walls of a patient's vessel. The lumen which is created between the drive assembly and the sheath is connected to a water pump within the Rotablator, and, in use, saline pumped through this lumen serves to lubricate and cool the rotating drive assembly.

The fiberoptic tachometer uses a fiber optic cable assembly for determining the rotational speed of the gas driven prime mover. Accordingly, there is no direct electrical connection between the Rotablator drive unit and any electrical power supply, thereby assuring complete patient isolation from electrical power supplies.

A control box is used to monitor the rotational speed of the angioplasty burr, with rate data (rpm) provided to the electronics by means of the fiber optic tachometer. A foot control may be used by the physician conducting the angioplasty, to turn on the prime mover, and a gas pressure regulator is used to control its rotational speed.

DETAILED DESCRIPTION OF THE PREFERRED EMBODIMENT

The contents of U.S. Pat. No. 4,646,736 entitled Transluminal Thrombectomy Apparatus which issued on Mar. 3, 1987 to D. C. Auth and U.S. Pat. No. 4,679,557 entitled Electrodynamic Transluminal Angioplasty System which issued to E. A. Opie, et al. on Jul. 14, 1987, are hereby incorporated by reference.

Figure 1:
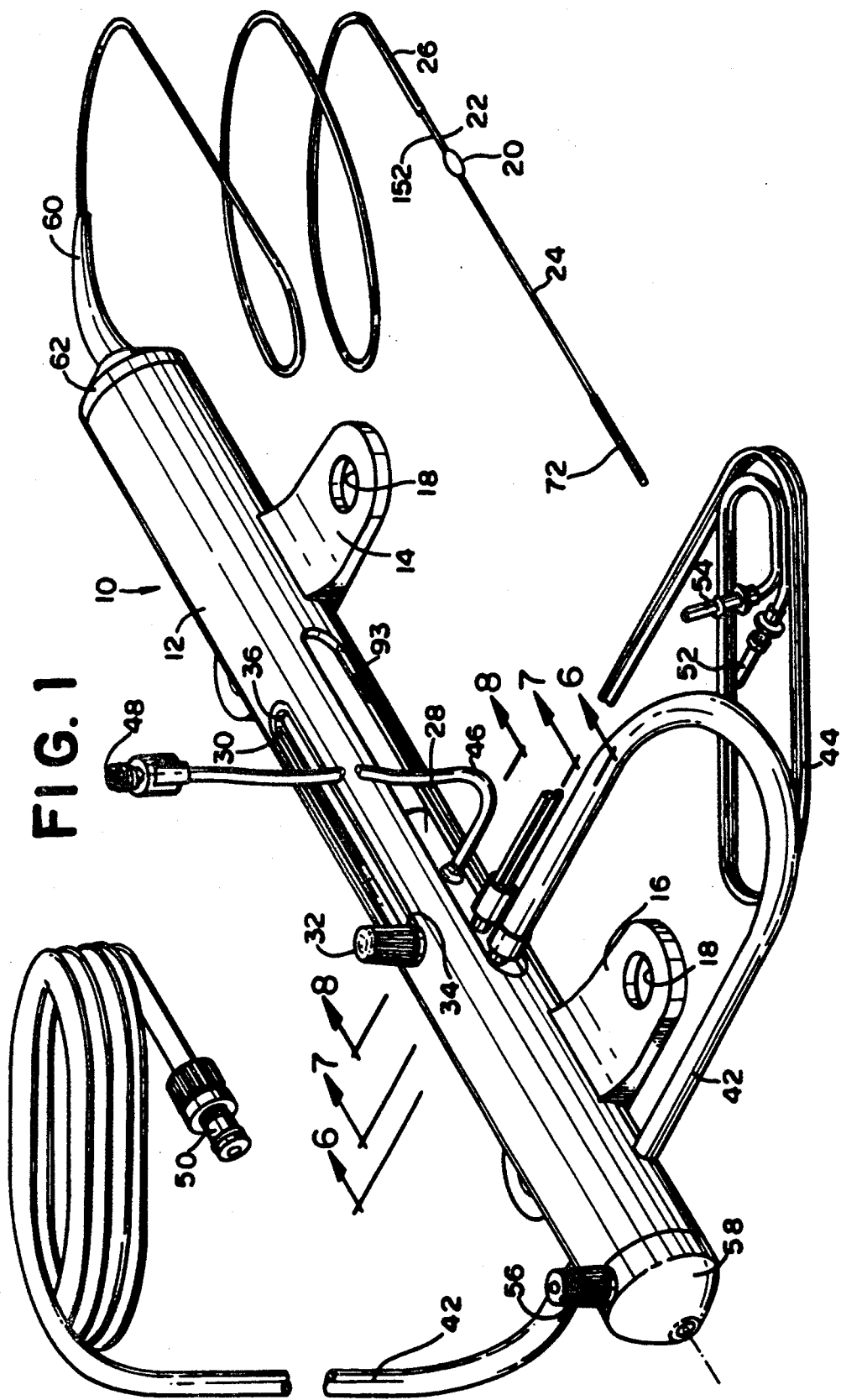
FIG. 1 is a perspective view of the Rotablator of the present invention.

Referring generally to FIG. 1, the Rotablator 10 of the present invention is shown. The Rotablator 10 is comprised of a substantially cylindrical body 12 having feet 14, 16 which hold it upright on the surface of a table. The feet 14, 16 are provided with openings 18 which may be used to secure the Rotablator 10 on a table during use. The components making up the body 12 and feet 14, 16 are comprised of a sterilizable plastic material, such as ABS plastic or a General Electric plastic called Ultem.

The Rotablator 10 is designed to power and control a rotating ablative burr assembly 20 of the type more fully described in co-pending U.S. application Ser. No. 816,190 filed Jan. 6, 1986 entitled TRANSLUMINAL MICRODISSECTION DEVICE and a continuation-in-part of that same application, Ser. No. 929,956 filed Nov. 12, 1986 now abandoned. In brief, the burr assembly 20 is an ellipsoidal, abrasive rotating burr which is affixed to a hollow, helical drive shaft 22 and guided over a guide wire assembly 24.

The helical drive shaft 22 is preferably made of a trifilar lay-up of vacuum melted 304 stainless steel with individual strands having a diameter of 0.006". The helix is preferably a "left-lay" and is rotated counterclockwise so as to tend to unwind, thereby avoiding "cinching" about the guide wire 24 and at the same time tending to shrink the drive shaft 22 in the longitudinal direction, so that as turning resistance is sensed by the distal cutting tip 20, the tip 20 automatically retracts or backs away. As such, this functions as a negative mechanical feedback system. This feature has been found to be useful in avoiding unstable mechanical failure or a tendency of the burr 20 and drive shaft 22 to dart or plunge.

The helical drive shaft 22 is housed within a hollow, plastic sheath 26. In the preferred embodiment, the lumen of the hollow helical drive shaft 22 is approximately 0.014" and thus rides with considerable clearance over the 0.009" central cylindrical guide wire rail 24. Preassembly lubrication with a biocompatible lubricant can further reduce friction, although successful utilization of the device can be obtained using nothing more than a saline infusion through the outer plastic sheath which provides cooling to the guidewire-helix interface, since the saline permeates through the helical strands. Saline is used because of its intravascular compatibility.

The helical drive shaft 22 is preferably glued to the burr 20 with a cyanoacrylate-type adhesive, and the left-lay helix tends to screw itself into the burr 20, further assuring against detachment of the burr 20 from the drive shaft 22 during operation. As will be obvious, the combination of right-lay and clockwise rotation would accomplish the same thing, both with respect to attachment of the burr 20 to the drive shaft 22 and the above discussion relating to anti-cinch and negative mechanical feedback.

As will be explained more fully hereinafter, the drive shaft 22 is driven by a gas driven prime mover. In the preferred embodiment of the invention, the gas driven prime mover is an air turbine housed within an advancer assembly 28 within the Rotablator body 12. As used herein, the term "air" is intended to include any gas suitable for driving a gas driven prime mover, such as air or nitrogen, and the term "air turbine" is meant to be representative of a gas driven prime mover, which may include either a turbine type prime mover or any other type of gas driven prime mover, e.g., a vane motor.

The advancer assembly 28 can be moved within the Rotablator body 12 over a range determined by the size of a slot 30 formed within the top of the Rotablator body 12. An advancer knob 32 is used to move the advancer assembly 28 within the advancer slot 30. The advancer knob 32 may be screwed down on the body 12 to frictionally lock the advancer assembly 28 in any desired position.

Figure 2:
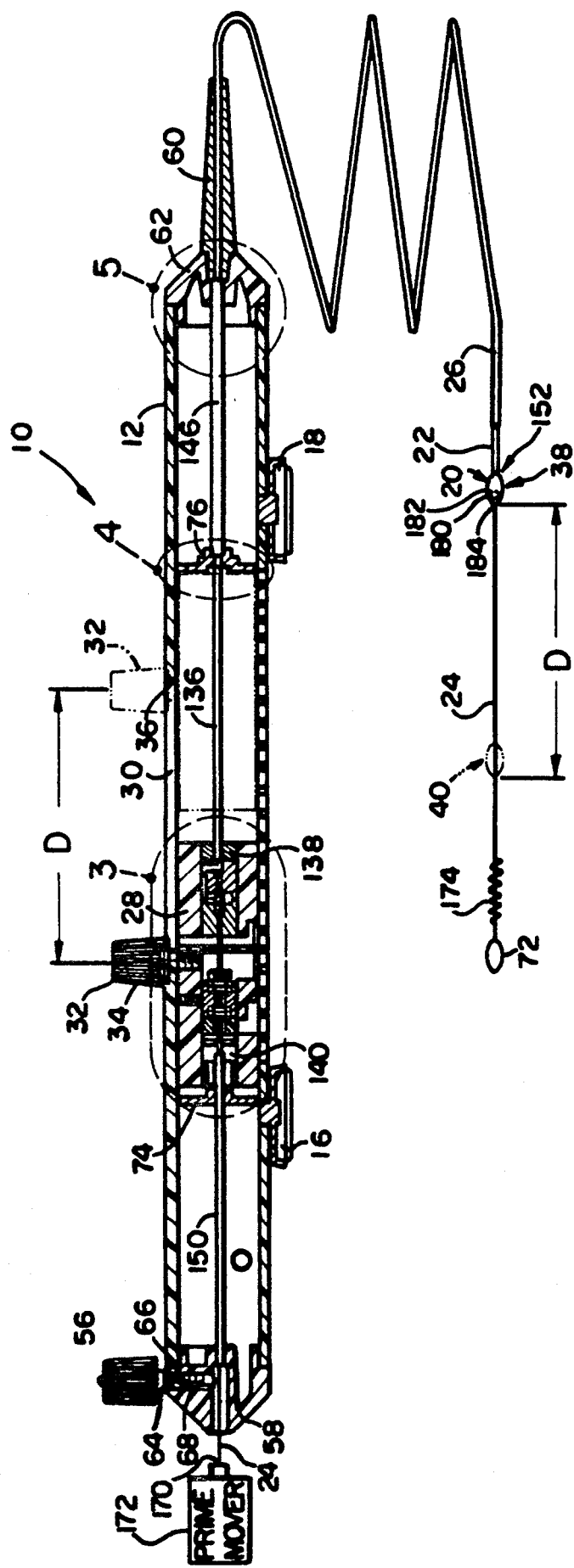
FIG. 2 is a cross-sectional view of the Rotablator assembly.

With reference to FIG. 2, as the advancer assembly 28 (shown in shadow in FIG. 2) is moved from the proximal end 34 (as shown in FIG. 1) of the advancer slot 30 to the distal end 36 of the advancer slot 30, (shown in shadow in FIG. 2) the burr assembly 20 is moved from a proximal position 38 on the guide wire assembly 24 to a distal position 40 thereon.

The air turbine located within the advancer assembly 28 is driven by means of a compressed gas, such as air or nitrogen, supplied through an air hose assembly 42 shown in FIG. 1. The rotational speed of the air turbine is determined by a fiberoptic tachometer. In the preferred embodiment, light from a fiberoptic cable is directed towards a reflective portion of the rotating turbine shaft is reflected back through a second fiberoptic cable (as will be explained more fully hereinafter) and electronically converted into a reading in revolutions per minute (rpm). Alternatively, a transmissive fiberoptic tachometer utilizing a flag which extends from the outer periphery of the tachometer rotor and periodically interrupts a light beam, or some similar arrangement, can be used. Accordingly, a fiberoptic cable assembly 44 is also connected to the advancer assembly 28.

In addition, an infusion system which permits saline solution, or other infusate, to be pumped through the sheath 26, in order to provide lubrication to the rotating drive shaft 22 located therein, is also included. An infusion hose 46 is connected to the advancer assembly 28 to permit saline to be pumped through the system, in a manner to be explained hereinafter. The infusion hose 46 has a hose connector 48 at its end remote from the advancer assembly 28. Similarly, the air hose assembly 42 has an air hose connector 50 at its end remote from the advancer assembly 28 and the fiberoptic cable assembly 44 has a pair of fiberoptic connectors 52, 54 at the end remote from the advancer assembly 28.

A brake knob assembly 56 is located on the rear portion of the Rotablator body 12, extending through a rear cap 58, and the sheath 26 extends through a strain relief 60 which is connected to a front cap 62 of the Rotablator body 12.

Referring now to FIG. 2, additional internal features of the Rotablator 10 are illustrated. As shown in FIG. 2, the brake knob assembly 56 is fitted into a threaded opening 64 in the rear cap 58. The threaded opening 64 receives a similar threaded portion 66 on the lower part of the brake knob 56. Within the opening 64 there is a brake plunger 68 which acts upon a flexible brake lining 70 (preferably polyurethane) when the brake knob assembly 56 is screwed down. When the brake lining 70 is clamped down thereon, the guide wire 24, which passes through the brake lining 70, is fixed in position. Accordingly, the brake knob assembly 56 is used to fix the position of the guide wire 24 thereby preventing the tip 72 at the distal end of the guide wire 24 from either rotating or from moving further into or out of the patient. As will be referred to below, the tip 72 may be either an atraumatic spring tip, as shown in FIG. 1, or a thrombectomy tip, as shown in FIG. 2.

Figure 3:
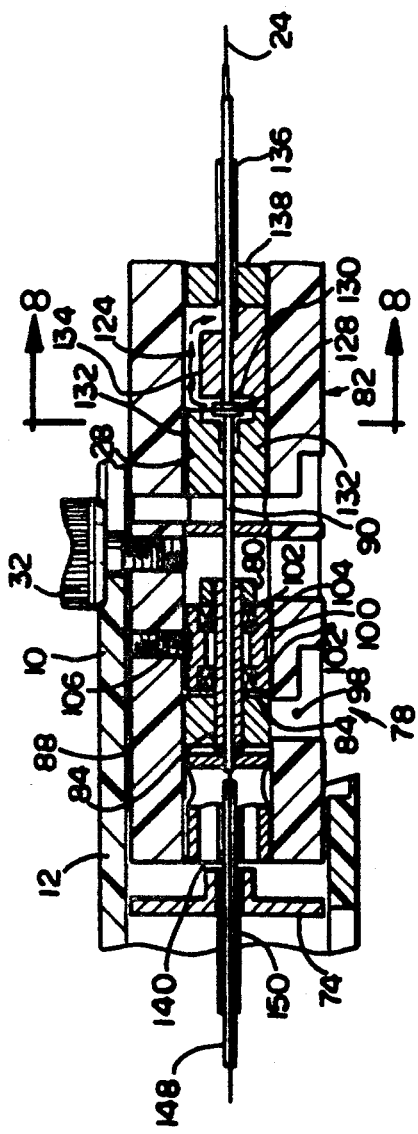
FIG. 3 is an enlarged cross-sectional view of the portion of the Rotablator assembly of FIG. 2 which is contained within the broken lines marked 3 on FIG. 2.

Also shown in FIG. 2 is the advancer assembly 28 (still greater detail is shown in FIG. 3). The advancer assembly 28 is movable within the Rotablator body 12 from the proximal end 34 (as illustrated) to the distal end 36 (shown in shadow) over a distance, D, corresponding to the movement both of the advancer assembly 28 and the burr assembly 20 along the guide wire 24. During movement of the advancer assembly 28 and burr assembly 20, the guide wire 24 remains in a fixed position as set by the brake knob assembly 56.

Figure 4:
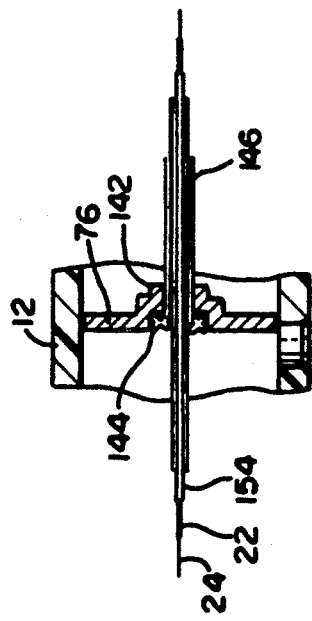
FIG. 4 is an enlarged cross-sectional view of the portion of the Rotablator assembly of FIG. 2 which is contained within the broken lines marked 4 on FIG. 2.

In moving from the proximal end 34 of the advancer slot 30 to the distal end 36 thereof, the advancer assembly 28 moves between a rear support 74, shown more fully in FIG. 3, and a front support 76, shown more fully in FIG. 4.

Figure 7:
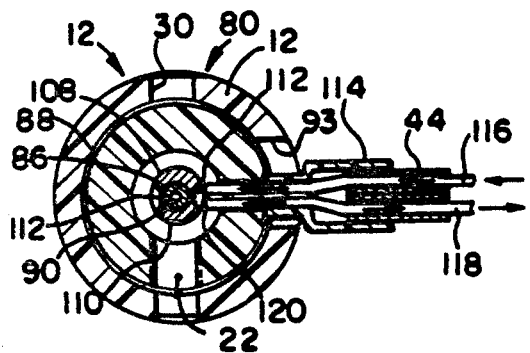
FIG. 7 is a cross-sectional view of the portion of the Rotablator assembly of FIG. 1 taken through the lines marked 7—7 on FIG. 1.
Figure 8:
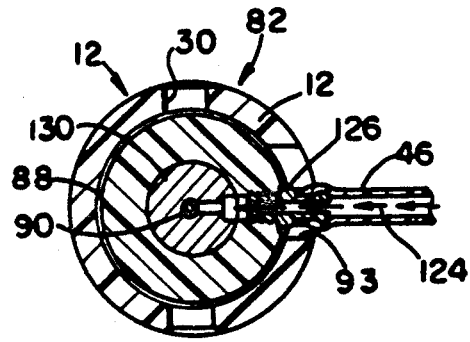
FIG. 8 is a cross-sectional view of the portion of the Rotablator assembly of FIG. 1 taken through the lines marked 8—8 on FIG. 1.

The advancer assembly 28 includes three main components, an air turbine 78 (shown more fully in FIG. 6), a tachometer 80 (shown more fully in FIG. 7), and a water pump 82 (shown more fully in FIG. 8).

Figure 6:
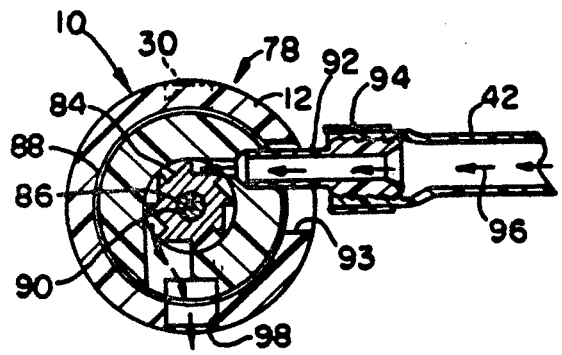
FIG. 6 is a cross-sectional view of the portion of the Rotablator assembly of FIG. 1 taken through the lines marked 6—6 on FIG. 1.

With reference to FIGS. 3 and 6, the air turbine 78 is comprised of a turbine rotor 84 mounted on a turbine shaft 86 within a turbine housing 88. The turbine housing 88 is actually part of the advancer assembly 28, so it slides within the Rotablator body 12 when the advancer assembly 28 moves forward or rearward. The turbine shaft 86 is mounted on a pump shaft 90, referred to below.

In operation, the air hose assembly 42 is connected to an air hose fitting 92 attached to the turbine housing 88 by means of a hose retaining ring 94. Air following an air path shown by the arrows 96 enters the turbine housing 88 and spins the turbine rotor 84 at high speed before exiting the turbine housing 88 through an exhaust port 98. The air hose fitting 92 extends through a slot 93 on the side of the Rotablator body 12.

With reference to FIG. 3, the turbine shaft 86 is held in place and rotates within a bearing housing 100. A pair of high-speed, miniature ball bearings 102 are mounted within the bearing housing 100 and are preloaded by means of wave washer 104. The bearing housing 100 is held within the turbine housing 88 by means of a set screw 106.

The air turbine nozzle is configured to provide the appropriate range of rpm and torque for the particular clinical use and size of burr which is being driven; i.e., as the burr size increases, more torque is needed for a given surface loading, and less rpm is needed to achieve the same surface feet per second. It is preferable to use at least 40 surface feet per second on the burr surface to achieve good cutting characteristics in soft tissue. On hard calcific tissue, 10 surface feet per second is adequate and provides a measure of differential cutting, thereby favoring the removal of hard tissue rather than soft when such a scenario is clinically advantageous. Thus, for example, to achieve 40 surface feet per second on a 1.5 mm diameter burr, an rpm of approximately 160,000 is required. To get 10 surface feet per second with the same burr requires only about 40,000 rpm. The operator can control the cutting characteristics by modulating the air turbine rpm. This may be done either by changing the air pressure provided to the turbine nozzle or by using an automatic speed control which senses instantaneous rpm and compares it to the preset desired value, automatically correcting the air supply to regulate the rpm. There would still be limits on the maximum torque that could be delivered in order to safeguard the patient against an overzealous angiographer or surgeon.

With reference to FIGS. 3 and 7, the tachometer 80 is comprised of a tachometer rotor 108 mounted within the turbine housing 88 on the turbine shaft 86 which surrounds the pump shaft 90. The tachometer rotor 108 has a dark exterior surface 110 which is substantially non-reflective. The tachometer rotor 108 includes two reflective areas 112 located on opposed sides of the tachometer rotor 108 preferably 180° apart in order to balance the rotor 108. However, any number of reflective areas can be used, with suitable adjustments to the electronics.

The fiberoptic cable assembly 44 is connected to the turbine housing 88 by means of a dual fiberoptic connector 114. The fiberoptic cable assembly 44 houses fiberoptic cables 116, 118 with one of the cables 116 carrying light into the turbine housing 88 and the other cable 118 carrying light out of the turbine housing 88. While the light shining through the cable 116 is continuously on, light coming out of the cable 118 is pulsed by reflective returns due to the rotation of the tachometer rotor 108. A pulse of light will appear each time one of the reflective areas 112 passes the end 120 of the fiberoptic cables 116, 118. The number of pulses received back in a given amount of time corresponds to the number of reflective areas 112 which pass the end 120 of the fiberoptic cables 116, 118. Accordingly, with two reflective areas 112 on the tachometer rotor 108, the number of light pulses received on fiberoptic cable 118 per minute corresponds to twice the rotation speed of the turbine shaft 86 in rpm. Accordingly, in order to determine the rotational speed of the turbine shaft in rpm, the number of light pulses coming out of the fiberoptic cable 118 is counted over a period of time, normalized to a minute, and that number is divided by the number of reflective areas 112 (in this case 2) to obtain the rpm of the turbine shaft 86. A vent and drain 122 is provided in the region adjacent to the tachometer 80.

The reflected pulses of light are returned via the fiber optic cable 44 to the monitor console (not shown) where a photodetector converts them to electrical pulses for conventional electronic counting.

Appropriate electronics are used to buffer and amplify the signal which drives a digital tachometer readout positioned on the monitor console. The digital readout is well illuminated to provide easy readability in a typical dimly-lit angiography suite. The rpm readout is very useful while performing rotational anioplasty, because the operator can visually discern tissue loading on the cutting burr 20. When the rpm drops by about 5-10%, the burr 20 is making good progress in its surgical excision of the atherosclerotic or thrombotic lesion. Sometimes, the operator is visually preoccupied with the progress of the procedure on the X-ray screen and cannot be distracted to look at the rpm display. Accordingly, a redundant audio signal which tells the angiographer the rotation rate in the form of an analog audio signal can be used. Thus, for example, at 120,000 rpm which is the same as 2000 rps (revolutions per second), an audible signal of 2000 Hz is generated. As the machine drops in rpm, the audio signal drops in frequency, and the angiographer is alerted to the relative level of engagement in the lesion. An additional divide-by-two circuit may be used to provide an acoustic signal which is half of the rps in order to bring the audio signal into a hearing range which is more easily perceived but is still directly and linearly proportional to the drive shaft rpm. The same analog perception of cutting-tip loading is perceived, and on the whole, a more satisfactory proprioceptive feedback is attained. The volume of the projected audio sound is adjustable for individual clinical preference. The monitor and control console contains a battery to supply electrical current for the tachometer display and the electronic rpm measurement and display circuitry.

With reference to FIGS. 3 and 8, the water pump 82 is used to pump saline solution from the infusion hose 46 between the sheath 26 and the drive shaft 22. Infusate, such as saline solution 124, enters the water pump 82 through the infusion hose 46. The infusion hose 46 is connected to the turbine housing 88 by means of a barbed fitting 126. The saline solution flows around the pump shaft 90 which is attached to the turbine shaft 86, as shown in FIG. 6. The pump shaft 90 is attached to a pump rotor 128 which is mounted within a cavity which rotates within a cavity 130, shown in FIG. 3.

Figure 5:
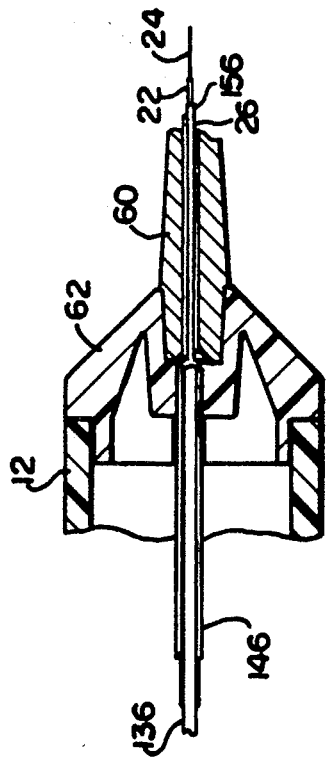
FIG. 5 is an enlarged cross-sectional view of the portion of the Rotablator assembly of FIG. 2 which is contained within the broken lines marked 5 on FIG. 2.

A rear pump seal 132 and a front pump seal 134 are mounted within the turbine housing 88. There is a path for saline to flow past the front pump seal 134 into a front plug tube assembly 136. The front plug tube assembly 136, also illustrated in FIG. 5, is used to permit movement of the advancer assembly 28. The front plug tube assembly 136 extends through, and is sealed to a front plug 138 at the front (distal end) of the turbine housing 88. The front plug tube assembly 136 is slidable within a front cap tube 146 which extends between the front support 76 and the front cap 62.

Similarly, a rear plug 140 is mounted at the rear (proximal end) of the turbine assembly 88. With reference to FIGS. 2 and 3, the rear support 74 is connected to the rear cap 58 by a rear cap tube 150 which permits a rear plug tube 148 to slide therethrough toward the rear cap 58. Thus, the advancer assembly 28 can slide both forward and rearward within the Rotablator body 12 while maintaining the seal, i.e., the front support 76 permits the front tube assembly 136 to be advanced into the front cap tube 146 when the advancer assembly 28 is moved forward and the rear cap tube 150 permits the rear plug tube assembly 148 to move rearward the advancer assembly 28 rearward.

If an atraumatic spring tip 72 (FIG. 1) is used, then it may be formable, so that it may be preformed. Such a tip is preferably radiopaque, so that it may be guided, typically under fluroscopy, through a patient's vessel. Alternatively, the thrombectomy tip 72 shown in FIG. 2 may be used. The thrombectomy tip 72 is preferably fabricated from platinum tubing, and is approximately 0.080" long×0.025" diameter. Cyanoacrylate adhesives have been found to be reliable for fastening the thrombectomy tip 72 to the guide wire rail 24. The platinum tip 72 has been found to provide good contrast visualization when viewed on a standard X-ray of the type used in a conventional catheterization lab.

In the preferred embodiment, the helical drive shaft 22 is bonded to the air turbine drive shaft 86 using cyanoacrylate glue. The air turbine rotor 84 is preferrably fabricated out of a plastic, such as Delrin, and, in conjunction with the drive shaft 22, burr 20, and tachometer target wheel 108, have a combined moment of inertia of approximately 0.05 g-cm$^2$ in the preferred embodiment. A low rotating inertia is important to prevent failure of the drive shaft 22 under abrupt load change (stall) conditions. When the rotating mass is too high, the inertial overrun can cause the drive shaft 22 to fail. Protection against failure secondary to abrupt stall conditions is necessary, since abrupt stall conditions can occur in clinical operation when the system is advanced too quickly into an obstruction. In fact, the limiting torque of the system acts as a safety feature which prevents excessive torque from being delivered to a patient's vessel. As the system begins to load up, the rpm drops, eventually reaching zero or stalling when the maximum torque is transmitted.

There are various areas of the helical drive 22 which have low friction heat shrink material, such as Teflon, applied thereon. These areas include the region 152, where the drive 22 exits from the sheath 26. In this region 152, the low friction heatshrink prevents the drive 22 from engaging the inner wall of a patient's vessel. In other regions 154, 156, where the drive 22 passes through the front support 76 and where it passes through the strain relief 60, the heatshrink reduces the friction on the rotating drive 22.

In the operation of the Rotablator 10, a physician advances the guide wire 24 into a patient's vessel in the manner in which a catheter guide wire would be conventionally advanced therethrough, typically under the aid of fluroscopy. The burr assembly 20 follows the guide wire 24. At the point where an obstruction is observed, the Rotablator 10 is turned on by stepping on a foot pedal which controls an air supply to the air hose 42. The turbine 78 can spin at speeds up to about 160,000 rpm as measured by the tachometer 80. Consequently, the burr assembly 20 spins at rotational speeds up to about 160,000 rpm. Abrasive particles on the burr 20 are advanced into an obstruction and are able to quickly abrade the obstruction.

In performing this procedure, the guide wire 24 will typically be locked in position using the brake knob assembly 56. Then, by suitable advancement of the advancer knob 32, the burr assembly 20 can be advanced through the obstruction at a rate determined by the operator. Saline solution which is pumped by the water pump 82 serves to lubricate the drive shaft 22 within the sheath 26 while the burr assembly 20 is spinning at high speeds.

Battery operation provides an extra measure of electrical isolation even though all of the cords (fiberoptic and air hoses) are electrical non-conductors. The console has its own built-in battery charger and battery charge level indicator to provide additional clinical convenience. Several procedures can be completed before an overnight charge cycle is required. The control console panel contains the gas pressure gauge which displays air turbine pressure (less line loss during flow). It also contains the pressure (rpm) adjustment regulator. This can be adjusted during a procedure by a non-sterile circulating nurse or assistant or, alternatively, a sterile plastic drape or cover can be placed over the pressure knob so that the angiographer or surgeon can control rpm on-line without compromising his/her sterility. A remote optically, acoustically, or electromagnetically coupled control system could be installed, if desired, to permit changing rpm from the patient table or at the location of the Rotablator body 12.

The Rotablator assembly 10 is constructed of inexpensive materials which can be thrown away after each intravascular procedure. It will be factory sterilized and delivered in a sterile package.

In order to make this system useful for thrombectomy or initial guide wire penetration of heavily obstructed or totally obstructed arteries where powered rotation of the guide wire/thrombectomy shaft is desired, a separate accessory has been designed which attaches to the guide wire. This drive unit provides relatively slow speed (approximately 5000 rpm) powered rotation of the guide wire atraumatic tip 72, thereby making it into an effective thrombectomy tip. This accessory thrombectomy converter allows expansion of the basic atherectomy system into a dual axis powered rotation system capable of both thrombectomy and atherectomy in a single throwaway system. When thrombectomy is not needed, the accessory thrombectomy converter is not used. The accessory thrombectomy converter preferably makes use of a pin vise attachment to the guide wire. Alternatively, one of several other conventional designs for quick disconnect engagement of rotating shafts, such as splines, facets, or rub wheels, can be used. The thrombectomy converter is preferably disposable containing its own electrical or gas energy storage cell and rotational prime mover with an on/off control.

The three coaxial linear elements 22, 24, 26, which enter the arterial lumen extend forward from the Rotablator body 12 connected independently to respective control or envelope elements contained within the Rotablator body 12. The outermost sheath 26 contains the high-speed helical drive 22, thereby shielding it from tissue, except for the portion extended from the distal aperture of the sheath. In the preferred embodiment, the inside diameter of the sheath housing 26 is at least 0.030" to accommodate the 0.026" outer diameter of the helical drive 22. The sheath 26 has a 0.054" outside diameter. With a 0.054" outside diameter, the sheath housing 26 easily threads within a standard angioplasty guiding sheath housing readily available from a variety of commercial sources. These angioplasty guiding sheaths are available in 8 or 9 French sizes meaning that the outside diameter is nominally 8/3 or 9/3 mm. With an 8 French commercial guiding sheath, the internal diameter is typically at least 0.065" meaning, that the 0.054" sheath housing passes through with room to spare. This extra room can be useful for injection of contrast media through the guiding sheath and is sometimes helpful for negotiating articulate bends within the guiding sheath where difficult anatomical terrain is traversed. Sometimes a considerably larger diameter sheath housing is used when the anatomy is more forgiving (i.e., larger gauge), and this then permits more adequate volumes of contrast injection directly through the sheath housing, rather than through the guiding sheath. When the system is used within a guiding sheath, there are four discrete coaxial components threaded within the artery.

The device described herein, is a clinically practical device which accommodates the needs of the parties involved: for the patient, it is safe and effective; for the physician, it is easy to use and understand; for the support staff, it is sterile, disposable and problem free; and for the manufacturer, it is buildable, testable, and reliable.

We claim:

1. A gas driven, rotary ablative apparatus for medical applications comprising:
   (a) a body having an advancer assembly which can be moved between a proximal position and a distal position;
   (b) a gas driven prime mover within said advancer assembly an movable therewith, said gas driven prime mover having a shaft which is attached to a first end of a rotatable, flexible, hollow, high-speed drive shaft;
   (c) an ablative burr attached to the second end of said flexible, hollow, high-speed drive shaft and movable between proximal and distal positions with said advancer assembly, said advancer assembly cooperating with said prime mover such that said ablative burr can be rotated at high speed while being advanced;
   (d) a flexible sheath which extends from one end of said body substantially along the length of said drive shaft, forming a lumen between said drive shaft and said sheath, whereby the inner walls of a patient's vessel into which said drive shaft is inserted will be isolated from said rotating drive shaft by said sheath; and
   (e) a water pump having a shaft connected to the prime mover drive shaft, the output of the water pump being in fluid connection with the lumen between said drive shaft and said sheath.

2. A gas driven, rotary ablative apparatus for medical applications comprising:
   (a) a body having an advancer assembly which can be moved between a proximal position and a distal position;
   (b) a gas driven prime mover within said advancer assembly and movable therewith, said gas driven prime mover having a shaft which is attached to a first end of a flexible, hollow, high speed drive;
   (c) a rotating ablative burr attached to the second end of said flexible, hollow, high-speed drive and movable between proximal and distal positions with said advancer assembly;
   (d) a flexible sheath which extends from one end of said body substantially along the length of said drive, whereby the inner walls of a patient's vessel into which said drive is inserted will be isolated from said rotating drive by said sheath; and
   (e) a water pump within said advancer assembly and movable therewith having a shaft connected to said prime mover shaft, the output of said water pump being connected to a lumen formed between said drive and said sheath.

3. The apparatus of claim 2, wherein said drive is comprised of a helical, spring-like winding.

4. The apparatus of claim 3, wherein said gas driven prime mover has a hollow shaft and said burr includes a central opening, whereby said burr and said drive can be fed along a guide wire into a patient's vessel.

5. The apparatus of claim 4, wherein said body includes brake means for preventing movement of said guide wire.

6. The apparatus of claim 5, wherein said brake means includes a brake knob which can be screwed into said body, a flexible tube through which said guide wire passes within said body, and a brake plunger which exerts pressure on said tube when said brake knob is screwed onto said body.

7. The apparatus of claim 4, wherein there is an atraumatic tip at the distal end of said guide wire, said atraumatic tip being adapted for ensnaring fibrin within a clot within a patient's vessel.

8. The apparatus of claim 7, wherein means for rotating said atraumatic tip is attachable to the proximal end of said guide wire.

9. The apparatus of claim 2, further comprising a fiberoptic tachometer, said fiberoptic tachometer comprising:
   (a) a tachometer rotor mounted on said prime mover shaft, said tachometer rotor having at least one reflective area thereon;
   (b) a pair of fiberoptic cables, one of which shines light onto said at least one reflective area, the other one of which carries reflected light pulses from said tachometer rotor; and (c) means for obtaining a count of said reflected light pulses and converting said count into revolutions per minute.

10. The apparatus of claim 9, wherein said body includes a slot formed therein for moving said advancer assembly within said body.

11. The apparatus of claim 10, wherein said advancer assembly includes means for attaching an air hose, a fiberoptic cable, and a source of infusate thereto.

12. The apparatus of claim 11, wherein said body has a slot formed therein for attaching said air hose, said fiberoptic cable, and said source of infusate.

13. The apparatus of claim 12, further comprising a lock means for locking the position of said advancer assembly within said body.

14. The apparatus of claim 13 further comprising a fixed front support means and a fixed rear support means within said body, said support means being adapted to define the distal and proximal limits of travel of said advancer assembly.

15. The apparatus of claim 14, wherein said advancer assembly includes tube means surrounding said drive and slidable over fixed tube means attached to said front and rear support means, whereby a continuous, sealed, telescopic tube extends from said advancer assembly to said sheath.

16. The apparatus of claim 12, further comprising means remote from said body for measuring the rotational speed of said gas driven prime mover.

17. The apparatus of claim 16, wherein said means for measuring the rotational speed of said gas driven prime mover comprises:
(a) a light supply means for supplying light through a first fiberoptic cable attached to said advancer assembly;
(b) light detecting means for counting light pulses arriving on a second fiberoptic cable attached to said advancer assembly; and
(c) converting means for converting said count into a measure of revolutions per minute by dividing said count per unit time by the number of reflective areas on said tachometer rotor.

18. The apparatus of claim 12, further comprising means for controlling the rotational speed of said gas driven prime mover comprising a source of compressed gas and means for regulating the flow of said compressed gas to said gas driven prime mover.

19. The apparatus of claim 18, further comprising operator control means for controlling the rotational speed of said gas driven prime mover.

20. The apparatus of claim 19, wherein said operator control means comprises a foot pedal which can be pressed by an operator, said operator control means causing said means for controlling the rotational speed of said gas driven prime mover to supply gas to said prime mover.

21. The apparatus of claim 2, further comprising a fiberoptic tachometer, said fiberoptic tachometer comprising:
(a) a tachometer rotor mounted on said prime mover shaft, said tachometer rotor having at least one means for interrupting a light beam thereon;
(b) a pair of fiberoptic cables, one of which shines light through the path through which said at least one means for interrupting a light beam passes, the other one of which carries transmitted pulses from said tachometer rotor; and
(c) means for obtaining a count of said transmitted light pulses and converting said count into revolutions per minute.

22. The apparatus of claim 21, wherein said body includes a slot formed therein for moving said advancer assembly within said body.

23. The apparatus of claim 22, wherein said advancer assembly includes means for attaching an air hose, a fiberoptic cable, and a source of infusate thereto.

24. The apparatus of claim 23, wherein said body has a slot formed therein for attaching said air hose, said fiberoptic cable, and said source of infusate.

25. The apparatus of claim 24, further comprising a lock means for locking the position of said advancer assembly within said body.

26. The apparatus of claim 25, further comprising a fixed front support means an fixed rear support means within said body, said support means being adapted to define the distal and proximal limits of travel of said advancer assembly.

27. The apparatus of claim 26, wherein said advancer assembly includes tube mean mounding said drive and slidable over fixed tube means attached to said front and rear support means, whereby a continuous, sealed, telescopic tube extends from said advancer assembly to said sheath.

28. The apparatus of claim 24, further comprising means remote from said body for/measuring the rotational speed of said gas driven prime mover.

29. The apparatus of claim 28, wherein said means for measuring the rotational speed of said gas driven prime mover comprises:
(a) a light supply means for supplying light through a first fiberoptic cable attached to said advancer assembly;
(b) light detecting means for counting light pulses arriving on a second fiberoptic cable attached to said advancer assembly; and
(c) converting means for converting said count into a measure of revolutions per minute by dividing said count per unit time by the number of reflective areas on said tachometer rotor.

30. The apparatus of claim 24, further comprising means for controlling the rotational speed of said gas driven prime mover comprising a source of compressed gas and means for regulating the flow of said compressed gas to said gas driven prime mover.

31. The apparatus of claim 30, further comprising operator control means for controlling the rotational speed of said gas driven prime mover.

32. The apparatus of claim 31, wherein said operator control means comprises a foot pedal which can be pressed by an operator, said operator control means causing said means for controlling the rotational speed of said gas driven prime mover to supply gas to said prime mover.

* * * * *

UNITED STATES PATENT AND TRADEMARK OFFICE
CERTIFICATE OF CORRECTION

PATENT NO. : 5,314,407
DATED : May 24, 1994
INVENTOR(S) : David C. Auth et al.

It is certified that error appears in the above-identified patent and that said Letters Patent is hereby corrected as shown below:

Column 11, Claim 12, line 2, "slot" should read -- a slot --.

Column 12, Claim 26, line 2, "an" should read -- and --.

Column 12, Claim 27, line 2, "mean" should read -- means --, and "mounding" should read -- surrounding --.

Column 12, Claim 28, line 2, "for/measuring" should read -- for measuring --.

Signed and Sealed this

Twenty-fourth Day of January, 1995

Attest:

BRUCE LEHMAN

*Attesting Officer*      *Commissioner of Patents and Trademarks*